(12) United States Patent
Buerk et al.

(10) Patent No.: US 10,007,104 B2
(45) Date of Patent: Jun. 26, 2018

(54) ENDOSCOPE AND METHOD FOR PRODUCING A DISTAL END OF AN ENDOSCOPE

(75) Inventors: Andre Buerk, Villingen-Schwenningen (DE); Peter Eisenkolb, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 468 days.

(21) Appl. No.: 13/588,665

(22) Filed: Aug. 17, 2012

(65) Prior Publication Data
US 2013/0046143 A1 Feb. 21, 2013

(30) Foreign Application Priority Data

Aug. 17, 2011 (DE) .................. 10 2011 081 067

(51) Int. Cl.
| | |
|---|---|
| A61B 1/00 | (2006.01) |
| G02B 23/24 | (2006.01) |
| A61B 1/06 | (2006.01) |
| A61B 1/04 | (2006.01) |

(52) U.S. Cl.
CPC ........ *G02B 23/2423* (2013.01); *A61B 1/0011* (2013.01); *A61B 1/00096* (2013.01); *A61B 1/00183* (2013.01); *A61B 1/0623* (2013.01); *Y10T 29/49826* (2015.01)

(58) Field of Classification Search
CPC ..... A61B 1/00183; A61B 1/0623; A61B 1/07; A61B 1/00096; A61B 1/0011; A61B 1/00167; A61B 1/00179; A61B 1/0607; A61B 1/0615; G02B 23/2423; G02B 23/2469; Y10T 29/49826

USPC ........ 600/129, 136, 160, 176, 173, 127, 175
See application file for complete search history.

(56) References Cited

U.S. PATENT DOCUMENTS

| | | | |
|---|---|---|---|
| 5,263,110 A | 11/1993 | Anderson | |
| 2004/0236183 A1* | 11/2004 | Durell | 600/173 |
| 2010/0063479 A1* | 3/2010 | Merdan et al. | 604/528 |
| 2010/0324372 A1* | 12/2010 | Buerk et al. | 600/176 |

FOREIGN PATENT DOCUMENTS

| | | |
|---|---|---|
| DE | 102009025660 A1 | 12/2010 |
| EP | 2263518 A1 | 12/2010 |

OTHER PUBLICATIONS

German Search Report; Application No. DE 10 2011 081 067.6; dated Oct. 7, 2011; 5 pages.

* cited by examiner

*Primary Examiner* — Timothy J Neal
(74) *Attorney, Agent, or Firm* — Whitmyer IP Group LLC (57) ABSTRACT

An endoscope includes an outer shaft with a distal end whose surface is configured by a cylindrical mantle surface and a curved front surface, such that the distal end of the outer shaft includes a mantle component and a curved front component that is joined to the mantle component. A distance of an interface between the mantle component and the front component from an edge between the mantle surface and the curved front surface is no greater than a wall thickness of the mantle component or no greater than a wall thickness of the front component.

16 Claims, 6 Drawing Sheets

Fig. 18

ENDOSCOPE AND METHOD FOR PRODUCING A DISTAL END OF AN ENDOSCOPE

CROSS-REFERENCE TO RELATED APPLICATIONS

The present application claims priority of German patent application No. 10 2011 081 067.6 filed on Aug. 17, 2011, the content of which is incorporated herein by reference.

FIELD OF THE INVENTION

The present invention relates to an endoscope, in particular the distal end of an outer shaft of an endoscope, and to a method for producing a distal end of an outer shaft for an endoscope.

BACKGROUND OF THE INVENTION

Many endoscopes have a viewing angle parallel to the longitudinal axis of their shaft. Increasingly, however, endoscopes with a different fixed viewing angle or with an adjustable viewing angle are demanded and are being developed. In addition, endoscopes with adjustable field of view or adjustable focal length and additional functions are in demand and are being developed. To include new fields of application, the shaft diameter is constantly being reduced. In the process, however, the need to provide the structural space necessary for devices of the observation beam path, of the illumination beam path, for adjusting the viewing angle, the field of view or other functions, constitutes a considerable challenge.

SUMMARY OF THE INVENTION

An object of the present invention consists in providing an improved endoscope and an improved method for producing a distal end of an outer shaft for an endoscope.

This and other objects are fulfilled through the content disclosed herein.

Refinements are indicated various embodiments disclosed herein, although not limited thereto.

Embodiments of the present invention are based on the idea of composing a distal end of an outer shaft for an endoscope from two surface components, namely a cylindrical mantle-shaped mantle component and a front component, which in particular has the shape of a surface that is curved only in one direction.

An endoscope may include an outer shaft with a distal end whose surface is made up of a mantle surface and a curved front surface, such that the distal end of the outer shaft includes a mantle component and a curved front component, which is joined to the mantle component, such that a distance of an interface between the mantle component and the front component of an edge between the mantle surface and the curved front surface is not greater than a wall thickness of the mantle component or no greater than a wall thickness of the front component.

The distal end of the outer shaft can be provided as a separately produced component that is then joined to the shaft tube or as a single piece from the start along with the shaft tube of the endoscope. The mantle surface of the distal end of the outer shaft may have in particular the shape of a cylindrical mantle with circular or other cross-section, such that all surface normals of the mantle surface are perpendicular to the longitudinal axis of the endoscope. The front surface or face may be in particular parallel to a predetermined angle perpendicular to the longitudinal axis of the endoscope. In particular, the front surface or face may be the shape of a portion of a mantle surface of a cylinder with circular or non-circular cross-section and axis of symmetry perpendicular to the longitudinal axis of the endoscope.

If the edge between the mantle surface and front surface is broken or rounded, or is beveled, then the distance to this edge may be understood to mean the distance to the line in which the mantle surface and front surface intersected one another, with the edge not broken or not rounded, or before breaking or rounding of the edge.

Both the mantle component and the front component may have a constant or essentially constant wall thickness, as is standard practice for example for components made of bent or elastically reshaped sheet metal.

A distance of the interfaces between mantle component and front component from the edge between mantle surface and front surface, which may be no greater than the wall thickness of the mantle component and/or no greater than the wall thickness of the front component, can be achieved, for example, with the features and production methods described hereafter, which make it possible to provide especially copious structural space inside the distal end of the outer shaft. In addition, it becomes possible in particular to produce the front component with comparative simplicity and thus at favorable cost.

In an endoscope as described here, the mantle component may constitute the entire mantle surface of the distal end of the shaft, apart from, at most, a border strip whose width is determined by the wall thickness of the front component.

Thus the mantle surface of the distal end of the outer shaft may be configured completely by a corresponding surface area of the mantle component, or a border strip along the edge between mantle surface and front surface, whose width corresponds to the wall thickness of the front component divided by the sine of the angle between mantle surface and front surface, is constituted by the front component and the rest of the mantle surface is constituted by the mantle component.

In an endoscope as described here, the front component can constitute the entire front surface of the distal end of the outer shaft, apart from openings in the front component.

Openings in the front component may be, in particular, an opening for a window component in the observation beam path and one or more openings for light outlet surfaces in the illuminating beam path of the endoscope.

In an endoscope as described here, the front component can constitute the entire front surface of the distal end of the outer shaft, apart from openings in the front component and apart from a border strip whose width may be determined by the wall thickness of the mantle component.

Thus the front surface of the distal end of the outer shaft, apart from openings in the front component, may be constituted completely by a corresponding surface area of the front component, or a border strip along the edge between mantle surface and front surface, whose width corresponds to the wall thickness of the mantle component divided by the sine of the angle between mantle surface and front surface, is constituted by the mantle component and the rest of the mantle surface is constitute by the front component.

As becomes clear, in particular, with reference to the examples described hereinafter, a front component that constitutes the entire front surface of the distal end of the outer shaft, apart from a border strip whose width may be determined by the wall thickness of the mantle component, can offer advantages concerning the joining of the front component to the jaw component. A front component that constitutes the entire front surface of the distal end of the outer shaft can provide especially ample surface for openings in the front component.

In an endoscope as described here, the front component may constitute a partial surface of the mantle surface and the mantle component may constitute a partial surface of the front surface of the distal end of the outer shaft.

In particular, the edge between mantle surface and front surface may be constituted partly by the mantle component and partly by the front component. In the area or areas in which the mantle component configures the edge, the mantle component may extend into the front surface, in particular in the form of a narrow strip whose width is determined by the wall thickness of the mantle component and the angle between mantle surface and front surface. In the area or areas in which the front component configures the edge, the front component may extend into the mantle surface, in particular in the form of a narrow strip whose width is determined by the wall thickness of the front component and the angle between mantle surface and front surface.

The borders between contiguous areas, in which the mantle component and the front component in alternation configure the edge between mantle surface and front surface, may permit a precise form-locked alignment of the front component in relation to the mantle component. In other words, these borders, before joining or during the joining process, may prevent any sliding of the front component in relation to the mantle component parallel to the edge between mantle surface and front surface. This can simplify production of the distal end and thus can reduce production costs. In addition, the achievable precision can be increased, which is significant in particular with respect to increasing miniaturization.

In an endoscope as described here, the front component may have, in particular, the shape of a surface with Gaussian curvature K=0.

A front component with the shape of a surface with disappearing Gaussian curvature can permit especially simple production, for example by bending a metallic surface in just one direction or by wire erosion. In addition, production is also possible by means of a cylindrical machining or grinding tool, which is required to be moved only along a single curve in a plane perpendicular to its rotation axis.

In an endoscope as described here, the front component may be configured, in particular, from an elastically shapable sheet metal.

Formation of the front component from a sheet metal curved in several directions (Gaussian curvature K≠0) and, in particular, formation of the front component from a sheet metal curved in one direction (disappearing Gaussian curvature K=0) can occur with the required precision and simultaneously at favorable cost. In addition, a small wall thickness can be achieved with an elastically shaped sheet metal, so that a good deal of useable structural space, in particular, remains in the interior of the distal end.

In one method for producing a distal end of an outer shaft for an endoscope, in which the surface of the distal end of the outer shaft is formed by a mantle surface and a curved front surface that adjoin one another on one edge, a mantle component is provided, a curved front component is provided and the front component is joined to the mantle component at an interface whose distance from the edge between mantle surface and front surface is no greater than a wall thickness of the mantle component or no greater than a wall thickness of the front component.

The mantle surface of the distal end of the outer shaft may have, in particular, the shape of a cylindrical mantle with a circular or non-circular cross-section, such that the surface normals of the mantle surface are perpendicular to the longitudinal axis of the endoscope, at least perpendicular to the longitudinal axis of the distal end of the outer surface of the endoscope. The surface normals of the curved front surface may have other orientations. In particular, all portions of the front surface may be parallel to a predetermined direction perpendicular to the longitudinal axis of the endoscope or of the distal end of the outer shaft of the endoscope. In particular, the front surface may have the shape of a portion of a cylindrical mantle with circular or non-circular cross-section and an axis of symmetry perpendicular to the longitudinal axis of the endoscope or of the distal end of the outer shaft.

If the edge between mantle surface and front surface is broken or rounded, the distance to this edge may be understood to mean the distance to the line in which mantle surface and front surface intersected with a non-broken or non-rounded edge.

With a method as described here, the production of the front component can include providing a workpiece and generation of the front component from the workpiece, at least either by means of erosion or of laser cutting.

The workpiece may be, in particular, a full cylinder with a cross-section that corresponds to the cross-section of the distal end of the outer shaft that is to be produced or else is somewhat greater than the said shaft. The front component, in particular, may be generated from the workpiece by means of wire erosion. Alternatively the front component can be produced, for example, by means of a machining method.

Precisely with a small cross-section of the distal end of the outer shaft that is to be produced and with a correspondingly small front component, the higher costs of erosion or of laser cutting, compared with other production methods, can have a minor significance. Producing the front component by means of erosion or laser cutting, however, can allow for a very high precision, as is required precisely for a front component for a distal end of an outer shaft with a small cross-section.

Alternatively, providing the front component can include producing a sheet metal and elastic shaping of the sheet metal.

In particular, the originally flat sheet metal may be reshaped only in one direction or in a plane so that the surface normals of the elastically shaped sheet metal are parallel to a predetermined plane or perpendicular to a predetermined straight line. Here, the elastically shaped metal may have the shape of a portion of a cylindrical mantle and a disappearing Gaussian curvature.

Elastic shaping of a metal plate can allow production of the front component in a manner that is especially cost-saving and simultaneously sufficiently precise.

With a method as described here, production of the front component can also include generation of a pass-through opening intended at least either to incorporate a light outlet surface in an illuminating beam path or a window component in an observation beam path.

One or more pass-through openings can be executed before or after the steps, described above, of erosion, laser cutting or elastic formation of a metal sheet. Generating pass-through openings before erosion or laser cutting can have the advantage that the workpiece at this point is easier to insert than the thin-walled front component. Before the elastic formation of a metal sheet, pass-through openings can be economically and precisely generated in the still level metal, for instance by punching, acid treatment, milling or erosion.

With a method as described here, the joining of the front component to the mantle component can include fastening the front component to the mantle component and subsequent joining of the front component with the mantle component along the entire interface between the mantle component and the front component.

Fastening the front component to the mantle component may occur, in particular, at several point-shaped sites or in several small areas and in particular by means of laser welding. The interface may have, in particular, the topology of a closed path or of a circular border. Joining the front component with the mantle component along the entire interface may be achieved in particular by means of laser welding.

One method to produce an endoscope includes providing a shaft tube and producing a distal end as described here, such that the mantle component is configured by a distal portion of the shaft tube or is produced separately and then joined to the shaft tube.

Embodiments of the present invention are based on the idea of producing a distal end of an outer shaft for an endoscope from a tube whose distal peripheral area is reshaped by crimping to the front surface or to part of the front surface of the distal end of the outer shaft.

An endoscope may include an outer shaft with a distal end whose surface is made up of a mantle surface and a curved front surface, such that at least a part of the mantle surface is configured from a tube and such that at least a part of the front surface is configured from a crimped area of the tube.

An outer shaft whose front surface is constituted from a crimped area of a tube, which also forms the mantle surface or part of the mantle surface, can make it possible to have a thin wall for the distal end of the outer shaft, which creates an especially large structural area inside the outer shaft. At the same time, it can be economical to crimp the border of a tube, assuming sufficient precision.

In an endoscope, part of the front surface of the outer shaft can be constituted by a crimped area of a tube and another part of the front surface can be constituted by a front component joined to the tube.

A combination of one or more crimped areas and of one or more front components joined to the tube, in particular to the crimped area, can be advantageous with respect to the achievable precision and/or with respect to production costs. For example, narrow portions of the front surface on the border can be configured by openings in the front surface or by crimped areas of the tube and other, wider or larger-surfaced areas of the front surface can be configured by a front component joined to the tube.

In an endoscope with an outer shaft whose front surface is configured at least partly by a crimped area of a tube, the front surface can comprise an opening in the crimped area that has been generated in the area that is to be crimped, even before the crimping of the area.

By generating the openings even before the crimping, it is possible to make the area that is to be crimped easier to shape. In addition depending on the geometric shape, the material and the method used the generation of an opening in an area that is to be crimped can be possible with less difficulty than generating an opening in an area already crimped. Subsequent processing of the opening after crimping can increase the level of precision that is reachable.

In an endoscope with an outer shaft whose front surface is configured at least partly by a crimped area of a tube, the front surface can comprise an opening in the crimped area that has been generated in the crimped area after the crimping.

Generation of an opening in the front surface of the outer shaft after crimping of an area of the tube can be advantageous in particular if, on the completed outer shaft, a crimped area on the border of the opening is narrow and/or the opening is small.

In one method to produce a distal end of an outer shaft for an endoscope, in which the surface of the distal end of the outer shaft is configured by a mantle surface and a curved front surface, at least a part of the mantle surface is configured from a tube and at least a part of the front surface is configured by crimping an area of the tube.

In one method for producing a distal end of an outer shaft, in which at least a part of the front surface is configured by crimping an area of the tube, it is possible before crimping to generate an opening in the area that is to be crimped.

In one method for producing a distal end of an outer shaft, in which at least a part of the front surface is configured by crimping an area of the tube, it is possible after crimping to generate an opening in the area that is to be crimped.

A border of an area of the tube that is to be crimped depending on the geometric shape and mechanical properties of the tube and of its material can be roughly shaped, in particular cut, even before crimping, such that fine processing occurs after crimping. Alternatively, the border of the area that is to be crimped can be shaped, in particular cut, before crimping in such a way that, in crimping, the desired shape of the border of the crimped area develops without an additional processing step. This applies as well for openings in the area to be crimped and/or in the crimped area of the border.

BRIEF DESCRIPTION OF THE DRAWINGS

Hereafter, embodiments are described in greater detail with reference to the appended drawings, which are as follows.

DETAILED DESCRIPTION OF THE INVENTION

Figure 1:
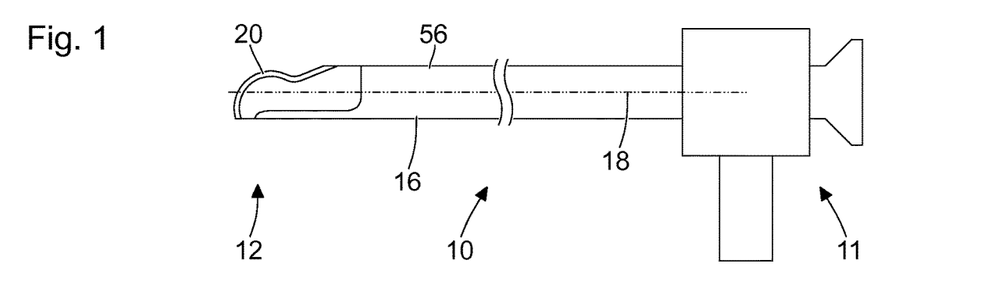
FIG. 1 shows a schematic depiction of an endoscope.

FIG. 1 shows one embodiment of a schematic depiction of an endoscope 10 with a proximal end 11 and a distal end 12. On the proximal end 11 of the endoscope 10, an eyepiece and a coupling are indicated for a light-conducting cable and are not described in further detail hereinafter. An outer shaft 16 extends from the proximal end 11 to the distal end 12 of the endoscope 10. The outer shaft 16 is configured in the illustrated example as straight and cylindrical, in particular circular-cylindrical. In the case of a cylindrical shape of the outer shaft 16, the longitudinal axis 18 of the endoscope is configured in particular by the aggregate of the surface center points or surface centers of gravity of the cross-section surface of the outer shaft 16. If the outer shaft 16 of the endoscope 10, contrary to the depiction in FIG. 1, is curved, then the longitudinal axis 18 is understood to mean the longitudinal axis at the distal end 12 of the endoscope 10.

In the endoscope illustrated in FIG. 1, the outer shaft 16 comprises a distal end 20, which is produced as a separate unit and thereafter is joined to the shaft tube 56 that predominantly constitutes the outer shaft 16. Embodiments of the distal end 20 of the outer shaft 16 and of its production method are described hereinafter with reference to the additional drawings.

Figure 2:
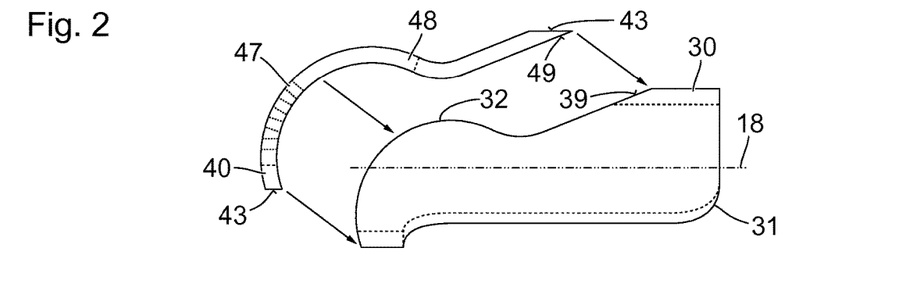
FIG. 2 shows a schematic depiction of an embodiment of the distal end of the endoscope from FIG. 1.
Figure 3:
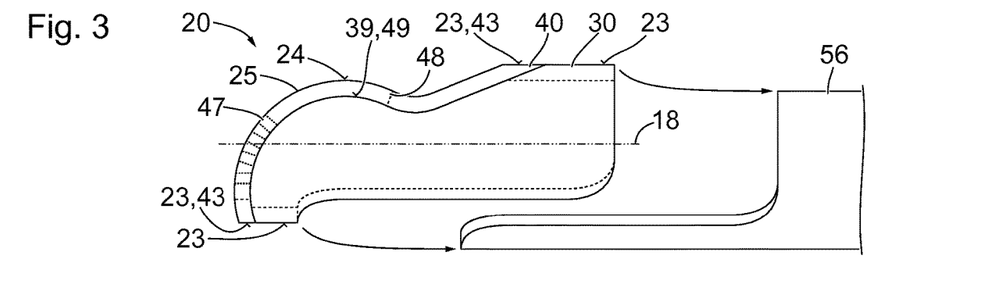
FIG. 3 shows another schematic depiction of the embodiment from FIG. 2.
Figure 4:
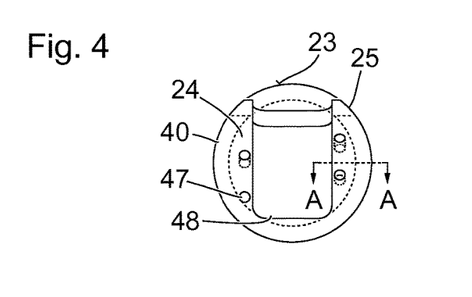
FIG. 4 shows another schematic depiction of the embodiment from FIGS. 2 and 3.
Figure 5:
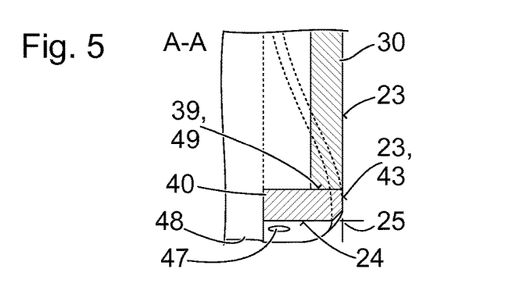
FIG. 5 shows a schematic depiction of an edge of the embodiment from FIGS. 2 through 4.

FIGS. 2 through 5 show schematic depictions of an embodiment of the distal end 20 of the endoscope 10 from FIG. 1. FIGS. 2 and 3 present drawings in which the planes of projection are parallel to the plane of projection of FIG. 1 and to the longitudinal axis 18 of the endoscope 10. The plane of projection of FIG. 4 is perpendicular to the planes of projection of FIGS. 1 through 3 and to the longitudinal axis 18 of the endoscope 10. FIG. 5 shows a schematic depiction of a section along a plane A-A parallel to the longitudinal axis 18 of the endoscope 10 and perpendicular to the planes of projection of FIGS. 1 through 4. The sectional plane A-A is indicated in FIG. 4. Contours are indicated in broken lines in FIGS. 2 through 5 that are actually not visible in the illustrations of FIGS. 2 through 4 or are situated in FIG. 5 between the observer and the sectional plane A-A.

FIG. 2 shows one embodiment of a schematic depiction of a mantle component 30 and of a front component 40 that are intended—as indicated by arrows in FIG. 2—to be combined and joined together. The mantle component 30 is cut from a tube with circular cross-section and accordingly has the shape of a section of a circular-cylindrical mantle surface. The proximal border 31 and the distal border 32 of the mantle component 30 are each situated in a separate plane. The shape of the proximal border 31 of the mantle component 30 is adjusted to the shape of the distal border of the shaft tube 56 shown in FIGS. 1 and 3. The shape of the distal border 32 of the mantle component 30 is adjusted to the shape of the front component 40 or corresponds to it.

The front component 40 has the shape of a section of a cylindrical mantle with non-circular cross-section and axis of symmetry perpendicular to the longitudinal axis 18 and to the plane of projection of FIG. 2, so that all surface normals of this section of the cylindrical mantle surface are parallel to the plane of projection of FIG. 2.

The front component 40 comprises on the border a surrounding strip-shaped border surface or border strip 43, which is intended and configured to constitute a part of the mantle surface of the completed distal end. In addition the front component 40 comprises several openings 47, intended and configured to be situated on the finished endoscope, each in a branch of an illuminating beam path, or to include a light outlet surface. In addition, the front component 40 comprises an opening 48, which is intended and configured to be situated on the finished endoscope in the observation beam path, in particular to include a window component with the shape of a section of a circular-cylindrical mantle. The extents and forms of the openings 47, 48 as well as their arrangement can be recognized in particular in FIG. 4.

As indicated by arrows in FIG. 2, the mantle component 30 and the front component 40 are intended to be placed together and joined in order to form the distal end 20 that can be recognized in FIG. 3. For joining them, in particular, an interface 39 is provided and configured on the mantle component 30 and a corresponding interface 49 on the front component 40. The interface 39 on the mantle component 30 and the interface 49 on the front component 40 each have in this embodiment the shape of a strip with varying width along the distal border 32 of the mantle component 30 or along the border of the front component 40. The interface 39 of the mantle component 30 and the interface 49 of the front component 40 are each parallel to the normals of the plane of projection of FIG. 2. In other words, all surface normals of the interface 39 of the mantle component 30 and of the interface 49 of the front component 40 are parallel to the plane of projection of FIG. 2.

FIG. 3 shows one embodiment of a schematic depiction of the distal end 20, which is made up of the components described above with reference to FIG. 2, namely the mantle component 30 and front component 40. The distal end 20 comprises a mantle surface 23, a front surface 24 and an edge 25 between the mantle surface 23 and the front surface 24. The mantle surface 23 has the shape of a section or of a portion of a circular-cylindrical mantle; therefore all surface normals of the mantle surface 23 are perpendicular to the longitudinal axis 18. The surface normals of the front surface 24 are parallel to the plane of projection of FIG. 3 or perpendicular to the surface normals of the plane of projection of FIG. 3. The edge 25 between the mantle surface 23 and front surface 24 is ring-shaped in structure. The mantle surface 23 is primarily configured by the mantle component 30 or by part of its surface. A narrow border area of the mantle surface 23 neighboring on the edge 25 is configured by a border surface 43 of the front component 40. The distance of the edge 25 from the interface 39, 49 between the mantle component 30 and the front component 40 (measured in the direction parallel to the local surface normals of the interface 39, 49) corresponds to the wall thickness of the front component 40. The width b of the strip-shaped border surface 43 varies depending on the angle α between the mantle surface 23 and the front surface 24 and is at least as large as the wall thickness d of the front component 40, $b = d/\sin(\alpha)$.

FIG. 3 shows, in addition, the distal end of the shaft tube 56. Arrows indicate how the distal end 20 can be attached on the shaft tube 56 in order to configure the outer shaft 16 (see also FIG. 1) for an endoscope.

The circular cross-section of the distal end 20 can be recognized in the schematic depiction in FIG. 4 with viewing angle parallel to the longitudinal axis 18 (compare FIGS. 1 through 3) toward the distal end 20. The only directly visible parts are the front component 40 and the front surface 24 formed by the front component 40 with openings 47 for partial strands of the illuminating beam path and an opening 48 for a window component in the observation beam path. In the illustrated projection, both the mantle surface 23 and the edge 25 between mantle surface 23 and front surface 24 appear as circles. Contours of the mantle component 30, not visible in FIG. 4, are indicated in broken lines.

FIG. 5 shows a schematic, enlarged depiction of a section along the plane A-A indicated in FIG. 4. In particular, in FIG. 5 the mantle component 30, the front component 40 and the interface 39, 49 between the mantle component 30 and the front component 40 can each be clearly recognized in the cross-section. In addition, an opening 47 in the illuminating beam path and the cut opening 48 in the observation beam path can be recognized.

In the enlarged depiction in FIG. 5, it can also be recognized that the edge between the mantle surface 23 and the front surface 24 is broken, or has a bevel. Alternatively, the edge can be rounded. As already mentioned, in this case the line of intersection between the continued mantle surface 23 and the continued front surface 24 can be considered as an edge 25 by which a distance of the interface 39, 49 is determined, for example. The continuations of the mantle surface 23 and of the front surface 24 are indicated in FIG. 5 by short straight lines, which cross at the point of intersection of the edge 25 with the plane A-A.

Figure 6:
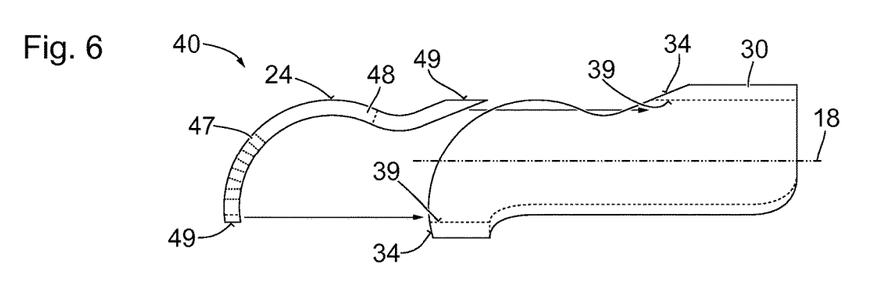
FIG. 6 shows a schematic depiction of another embodiment of the distal end of the endoscope from FIG. 1.
Figure 7:
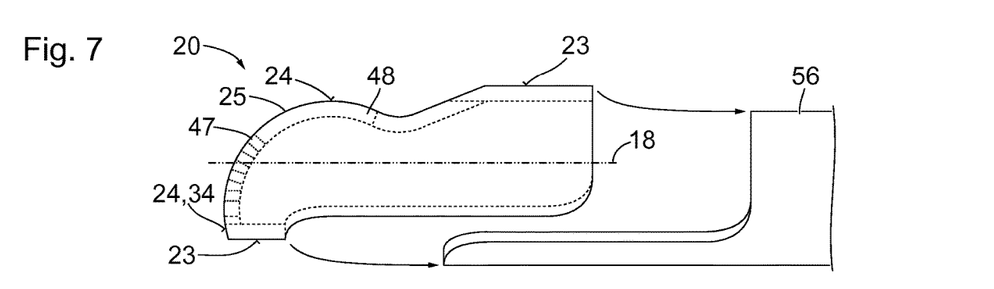
FIG. 7 shows another schematic depiction of the embodiment from FIG. 6.
Figure 8:
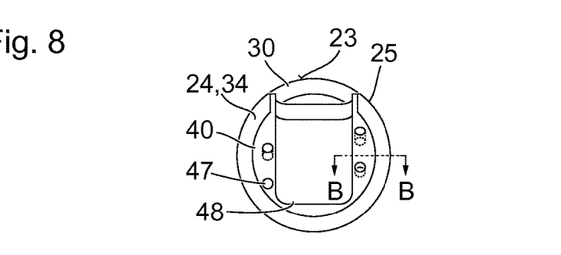
FIG. 8 shows another schematic depiction of the embodiment from FIGS. 6 and 7.
Figure 9:
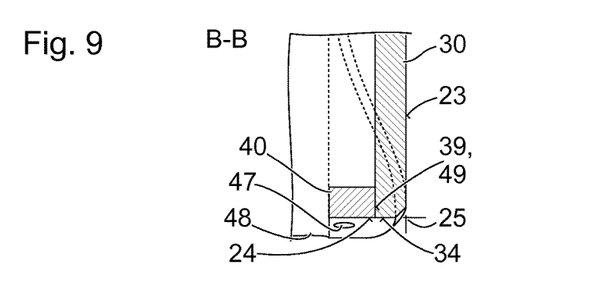
FIG. 9 shows a schematic depiction of an edge of the embodiment from FIGS. 6 through 8.

FIGS. 6 through 8 show schematic depictions of an additional embodiment of the distal end 20 of the outer shaft 16 of the endoscope 10 described above with reference to FIG. 1. FIGS. 2 and 6, 3 and 7, 4 and 8, 5 and 9 correspond with one another with respect to the type of depiction and plane of projection or the sectional plane.

The embodiment in FIGS. 6 through 9 resembles in some features the embodiment in FIGS. 2 through 5. In particular, in FIGS. 6 and 9 differences can be recognized in comparison to FIGS. 2 and 5. In the embodiment in FIGS. 6 through 9, the mantle component 30 extends to the front surface 24 of the distal end 20. The entire mantle surface 23 of the distal end 20 is thus configured by a portion of the surface of the mantle component 30. A strip-shaped facing surface 34 of the mantle component 30 forms in addition, bordering on the edge 25, a narrow, surrounding border strip of the front surface 24 of the distal end. Accordingly, the interface 39 of the mantle component 30 and the interface 49 of the front component 40 each have the shape of a strip-shaped portion, with ring-shaped structure, of a circular-cylindrical mantle. In other words, the interfaces 39, 49 of the mantle component 30 and of the front component 40 are parallel to the mantle surface 23 and to the longitudinal axis 18 in the embodiment in FIGS. 6 through 9. A consequence is that in the depiction in FIG. 8, besides the front component 40, the facing surface 34 of the mantle component 30 is also directly visible.

In the embodiments in FIGS. 2 through 9, it is expected that the distal end 20 is produced as a separate component and thereafter attached to the shaft tube 56 shown in FIGS. 1, 3 and 7 and joined with it. This allows, in particular, application of devices of the observation beam path, devices of the illuminating beam path and other devices not shown in FIGS. 1 through 9, before the joining of the distal end 20 to the shaft tube 56.

Alternatively, the mantle component 30 and the shaft tube 56 are produced from the start as a single unit. Thereby the number of interfaces and of joining processes can be reduced.

Figure 10:
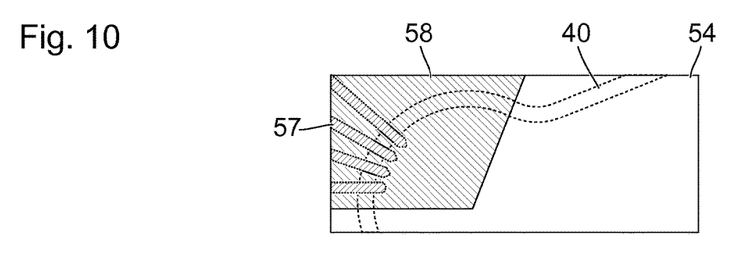
FIG. 10 shows a schematic depiction of an embodiment of the front component from FIGS. 2 through 5.

FIG. 10 shows a schematic depiction of a workpiece 54 from which the front component 40 of the embodiment from FIGS. 2 through 5 can be generated. The workpiece 54, in particular, originally has the shape of a full cylinder with the cross-section of the distal end 20 that is to be generated, or a somewhat greater cross-section.

First, in the workpiece 54 recesses 57 (in particular, circular-cylindrical boreholes) are generated for the openings 47 for the illuminating beam path and a recess 58 is generated for the opening 48 in the observation beam path (compare FIGS. 2 through 5). The recesses 57, 58 are generated in particular by means of a machining method or by an erosion process. Then the contour of the front component 40, illustrated in broken lines in FIG. 10, is generated by wire erosion, such that the wire runs perpendicular to the plane of projection of FIG. 10. Alternatively, the front component 40 is generated from the workpiece 54 by laser cutting or by means of a machining method. The openings 57 58, alternatively, can be generated partly or completely after generation of the contour of the front component 40 indicated in broken lines in FIG. 10.

Figure 11:
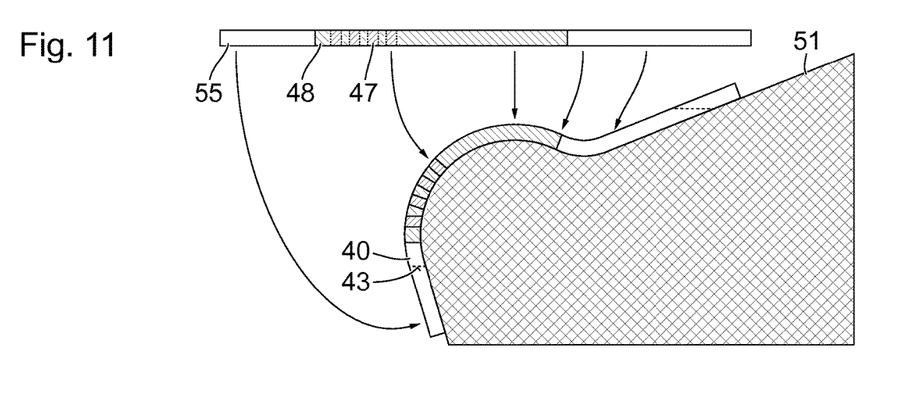
FIG. 11 shows a schematic depiction of another embodiment of the front component from FIGS. 2 through 5.

FIG. 11 shows a schematic depiction of a matrix 51, a sheet metal 55 and the front component 40 generated by means of the matrix 51 by elastic shaping of the metal 55, for the embodiment from FIGS. 2 through 5. The plane of projection of FIG. 11 is parallel to the planes of projection of FIGS. 1 through 3. Arrows in FIG. 11 indicate how the metal 55 is elastically shaped. The openings 47, 48 for the illuminating beam path and for partial strands of the observation beam path, as indicated in FIG. 11, can be generated in the metal 55 before it is elastically shaped, for example by punching, acid treatment, erosion, laser cutting or by means of a machining method. Alternatively, the openings 47, 48, contrary to the depiction in FIG. 11, can be generated only after elastic shaping of the metal 55.

The border surface 43 indicated in broken lines in FIG. 11 is generated after elastic shaping of the metal 55, before or after the joining of the front component 40 to the mantle component 30 (compare FIG. 2), for example by erosion, laser cutting or grinding.

Figure 12:
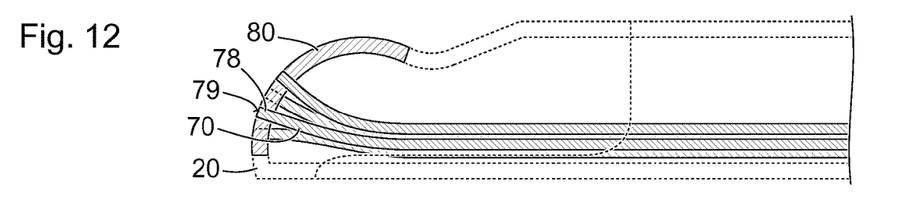
FIG. 12 shows a schematic depiction of devices of the illuminating and observation beam path.

FIG. 12 shows a schematic depiction of light conductors 70 and of a window component 80, which can be inserted in the distal end 20 according to one of the embodiments from FIGS. 2 through 11. The plane of projection of FIG. 12 corresponds to the planes of projection of FIGS. 1 through 3, 6, 7, 10 and 11 or is parallel to them. The distal end 20 and the shaft tube of the outer shaft connecting proximally are indicated only in broken lines. On the basis of the viewing angle that determines the depiction in FIG. 12, the distal ends 78 of two light conductors 70 are positioned in front of the window component and the distal ends of two additional light conductors 70 are placed behind it.

The light conductors 70 form or define partial strands of an illuminating beam path for conducting illuminating light. In particular, each light conductor 70 includes a bundle of pliable glass fibers or other lightwave conductors. Distal ends 78 of the light conductors 70 are each inserted into one of the openings 47 that can be recognized in particular in FIGS. 2 through 9. Light outlet surfaces 79 of the light conductors 70 are configured, in particular, flush or essentially flush with the front surface 24 (compare in particular FIGS. 3 and 7). The light outlet surfaces 79, after insertion and cementing or other joining of the distal ends 78 of the light conductors 70, can each be generated in one opening 47 of the front component 40 by grinding or polishing.

The window component 80 forms a component of an observation beam path for conducting or transmitting light that emanates from an object that is to be observed by means of the endoscope 10 (compare FIG. 1). The window component 80, similarly as the front component 40 (compare in particular FIGS. 2, 3, 6), has the shape of a section of a cylindrical mantle. In particular, the window component 80 has the shape of a circular-cylindrical mantle. Alternatively, the window component has the shape of a portion of a surface of an ellipsoid, in particular of a spherical surface. With the shape of a section of a circular-cylindrical mantle or an ellipsoid, the window component 80 is especially suited for an endoscope with adjustable viewing angle.

Figure 13:
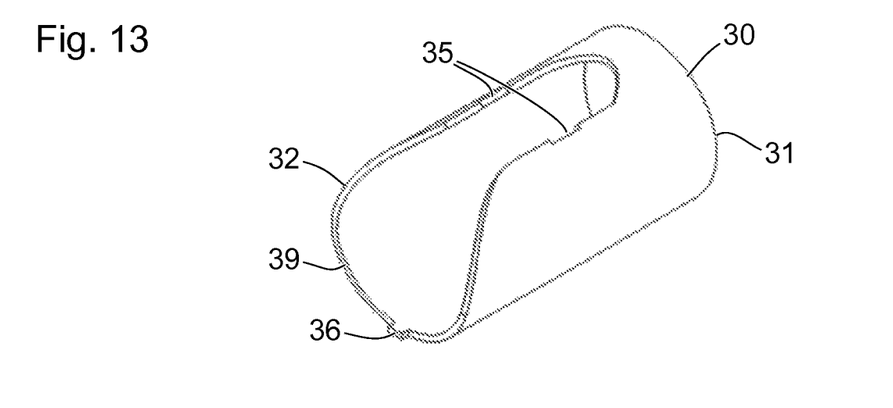
FIG. 13 shows a schematic depiction of a mantle component according to another embodiment.
Figure 14:
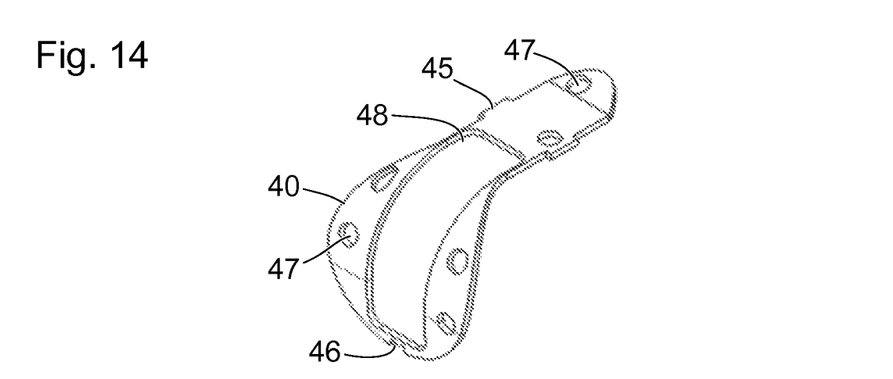
FIG. 14 shows a schematic depiction of a front component according to the embodiment from FIG. 13.
Figure 15:
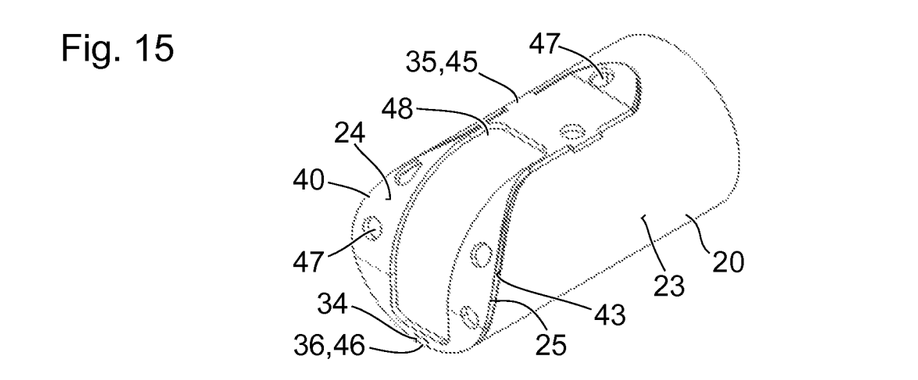
FIG. 15 shows a schematic depiction of a distal end of an outer shaft according to the embodiment from FIGS. 13 and 14.

FIGS. 13 through 15 show schematic axonometric depictions of an additional embodiment of a distal end 20 for an outer shaft 16 of an endoscope 10, as is described above with reference to FIG. 1. The distal end 20 includes a mantle component 30, which is shown in FIG. 13, and a front component 40, shown in FIG. 14. FIG. 15 shows the front component 40 attached to the mantle component 30. The front component 40, in particular similarly as described above with reference to FIG. 11 is produced by elastic shaping of an originally level sheet metal, such that the openings 47, 48 can be made in the still level sheet metal by punching, acid treatment, laser cutting or other means, even before the elastic shaping.

The embodiment in FIGS. 13 through 15 shows that the edge 25 between mantle surface 23 and front surface 24 can be configured not only either exclusively by the mantle component 30 or exclusively by the front component 40. In the embodiment in FIGS. 13 through 15, the edge 25 is, in particular, formed distally primarily by the front component 40. The front component 40, however, comprises a recess 46 into which a prong or a protrusion 36 on the distal border 32 of the mantle component 30 engages. In the area of the prong or protrusion 36, the mantle component 30 forms the edge 25.

In addition, in a proximal area the mantle component 30 comprises recesses 35, into each of which a prong or protrusion 45 on the front component 40 engages. In the proximal area in the vicinity of the recess 35, the edge 25 is configured primarily by the mantle component 30 or by a solder or welding seam, which for example is not yet present in the condition shown in FIG. 15. In the area of a recess 35 and of a protrusion 45 itself, the edge in each case is configured by the protrusion 45. Thus the protrusions 45 are shown in FIG. 15 still extending slightly beyond the mantle surface 24. These extensions are removed, for example by grinding or lathing, after the joining of the front component 40 to the mantle component 30.

The recesses 35, 46 and the corresponding protrusions 36, 45 that engage into them provide a form-locking connection between the mantle component 30 and the front component 40. This form-locking can precisely define the relative arrangement and orientation of mantle component 30 and front component 40. Thereby the production of the distal end 20 can be simplified and the precision that can be achieved thereby can be increased.

Figure 16:
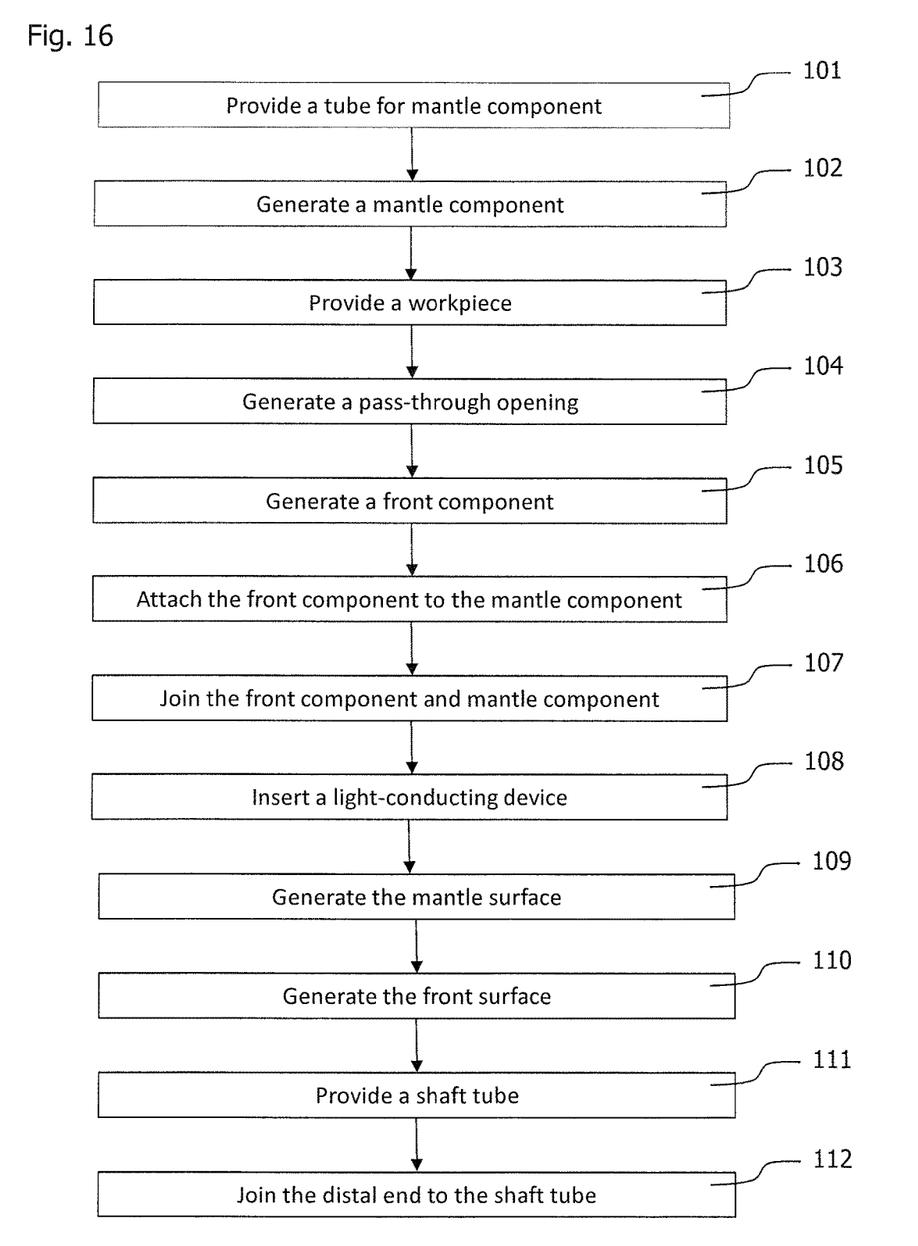
FIG. 16 shows a schematic flow diagram of a method for producing a distal end for an endoscope.

FIG. 16 shows a schematic flow diagram of a method for producing an endoscope. The method illustrated in FIG. 16 is also suited for producing distal ends of outer shafts that have features and properties that differ from the embodiments described above with reference to FIGS. 1 through 15. Nevertheless, reference numbers from FIGS. 1 through 15 are used hereinafter for the sake of clarity.

In a first step 101, a tube is provided from which a mantle component is to be generated. In a second step 102, from the tube provided in the first step 101, a mantle component 30 is generated, in particular by generation of a proximal border 31 and of a distal border 32.

In a third step 103, a workpiece 54 is provided from which a front component is to be generated. In a fourth step 104, recesses 57, 58 are generated that configure pass-through openings 47, 48 on the completed front component 40. In a fifth step 105, the front component 40 is generated from the workpiece 54, in particular by wire erosion, laser cutting or by means of a machining method. Contrary to the depiction in FIG. 16, pass-through openings 57, 58 can be generated in the front component 40 after the fifth step 105.

In a sixth step 106, the front component 40 generated in the third step 103, fourth step 104 and fifth step 105 is attached to the mantle component 30 generated in the first step 101 and second step 102, in particular by laser welding at several points or in several small areas. In a seventh step 107, the front component 40 and the mantle component 30 are joined. Here, in particular, a surrounding interface 39 on the mantle component 30 and a corresponding surrounding interface 49 on the front component 40 are joined. The interface 39, 49 between mantle component 30 and front component 40 has a distance from an edge 25 between a mantle surface 23 and a front surface 24 of the end 20 of the outer shaft 16 that is no greater than the wall thickness of the mantle component 30 or no greater than the wall thickness of the front component 40.

In an eighth step 108, a light-conducting device made of one or more light conductors 70 is inserted into the distal end 20. In the process, in particular, bundles of light-conducting fibers are inserted in pass-through openings 47 in the front component 40 and are glued or cemented there, for example. In a ninth step 109, the mantle surface 23 of the distal end 20 is generated or processed, in particular by lathing or grinding. The ninth step 109, contrary to the depiction in FIG. 16, can be performed before the eighth step 108. In a tenth step 110, a front surface 24 of the distal end 20 is generated, in particularly by grinding. In the process, light outlet surfaces 79 can simultaneously be generated by bundles of light-conducting fibers inserted in the eighth step 108, in particular by polishing.

In an eleventh step 111, a shaft tube 56 is provided. In a twelfth step 112, the distal end 20 is joined to the shaft tube 56 in order to configure an outer shaft 16 for an endoscope 10. Alternatively and departing from the depiction in FIG. 16, the distal end 20 or its mantle component 30 can be produced from the beginning as a single unit with the shaft tube 56. In this case, in particular, the twelfth step 112 is dispensed with.

Figure 17:
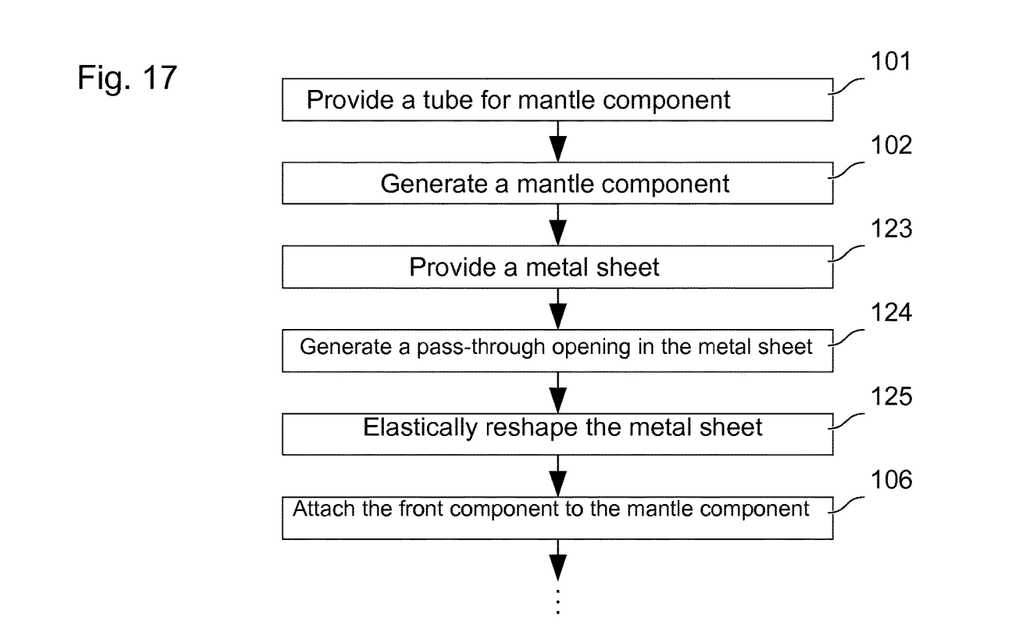
FIG. 17 shows a schematic flow diagram of another method for producing a distal end for an endoscope.

FIG. 17 shows a schematic flow diagram of an additional method for producing an endoscope. The first step 101, second step 102 and the steps starting with the sixth 106 correspond to the steps with the same names or described with reference to FIG. 16. The method illustrated in FIG. 17 is distinguished from the method shown in FIG. 16 in the third step 123, fourth step 124 and fifth step 125.

In the third step 123, a metal sheet 55 is provided that, in particular, is at first level. In the fourth step 124, one or more pass-through openings 47, 48 are generated in the metal sheet 55. In the fifth step 125, the metal 55 is elastically reshaped in order to configure the front component 40, in particular by means of a matrix 51. Alternatively, contrary to the depiction in FIG. 17, the sequence of the fourth step 124 and fifth step 125 can be reversed.

In the two methods illustrated by FIGS. 16 and 17, a few steps in the method are optional, for example the sixth step 106.

Figure 18:
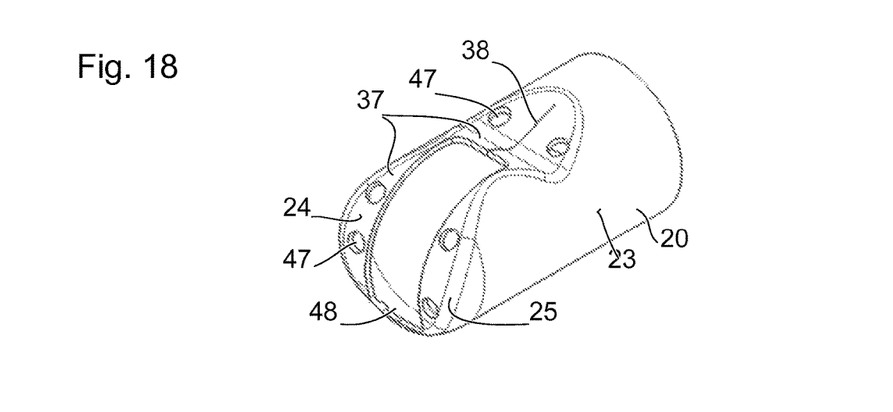
FIG. 18 shows a schematic depiction of another embodiment of the distal end of the endoscope from FIG. 1.

FIG. 18 shows a schematic axonometric depiction of an additional embodiment of a distal end 20 for an outer shaft 16 of an endoscope 10, as is presented above with reference to FIG. 1. The embodiment in FIG. 18 resembles in a few features the embodiments in FIGS. 2 through 9 and 13 through 15, in particular with respect to the arrangement of the openings 47 for an illuminating beam path and the arrangement and shape of an opening 48 for an observation beam path.

The distal end 20 for an outer shaft 16 of an endoscope 20, illustrated in FIG. 18, is distinguished from the embodiments in FIGS. 2 through 9 and 13 through 15 in particular in that both the mantle surface 23 and the front surface 24 are configured from a tube or a single tubular piece. The mantle surface 23 is configured by the unchanged tube. The front surface 24 is configured by crimped areas 37 of the tube.

Close to the distal border of the opening 48 for a window component in the observation beam path, shown in FIG. 18 below, the crimped area 37 is very narrow. Under some conditions it is possible to dispense entirely with crimping in this area, in particular if a suitable joining method is used to insert the window component in the opening 48 and if the opening 48 and the window component that is to be inserted have a suitable shape.

To the side of the opening 48, crimped areas 37 of varying width are provided, which in addition can each comprise one or more openings 47 for an illuminating beam path. Between these crimped areas 37 to the side of the opening 48 and of the mantle surface 23, a rounded edge 25 can also be recognized. Rounding of the edge 25 can simplify the crimping process and can be advantageous with respect to the firmness of the material of the tube that prevails after crimping.

Proximally and laterally from the opening 48 there is a relatively extensive crimped area 37. To reduce the amount of buckling required in crimping of this area 37, a seam 38 can be provided at which two borders of the tube, which were approximately V-shaped before crimping, run up against one another and are joined after crimping.

In producing the distal end 20 shown in FIG. 18, the openings 47 or part of the openings and the border of the opening 48 can be generated even before crimping in the areas of the as yet uncrimped tube that are to be crimped. In generating the openings 47 and the border, care is to be taken that they are reshaped during crimping, in particular that they can be exposed to buckling, shearing and stretching. To increase geometric precision, both the openings 47 and the border of the opening 48 can be reprocessed after crimping. Alternatively, the openings 47 or part of the openings 47 and/or the border 48 can be generated only after crimping.

Alternatively, departing from the depiction in FIG. 18, part of the front surface can be configured by a front component that is first separately produced and then joined to the tube. For example, the areas of the front surface 24 situated laterally from the opening 48 are generated by crimping, and the greater area proximally from the opening 48 is configured at least partly by a front component. This front component can extend to the edge 25 between mantle surface 23 and front surface 24 and can be joined directly with uncrimped areas of the tube. In addition, the front component can be joined with crimped areas of the tube alternatively or at other points.

To generate or process the openings 47 or the border 48, machining methods such as boring, milling or grinding or other methods such as laser cutting, punching, wire erosion can be used, depending on whether they are used before or after crimping.

What is claimed is:

1. An endoscope comprising:
an outer shaft composed of a shaft tube and a separately produced distal end unit, the shaft tube forming a majority of the outer shaft, the distal end unit being joined to the shaft tube,
the distal end unit having a mantle surface, a curved front surface, and an edge between the mantle surface and the curved front surface,
the distal end unit comprising a mantle component and a curved front component which is joined to the mantle component at an interface,
wherein the mantle surface is formed by a surface of the mantle component and border strip of the front component, and wherein the curved front surface is formed by the front component,
wherein a distance from the interface to the edge is no greater than a wall thickness of the mantle component or no greater than a wall thickness of the front component,
wherein the distance is measured in a direction of a local surface normal of the interface,
wherein, in the case of the edge is broken, rounded, or beveled, the distance from the interface to the edge is a distance to a line in which the mantle surface and the curved front surface intersect when the edge is not broken, rounded or beveled, or before the edge is broken, rounded, or beveled,
wherein the front component forms the entire front surface of the distal end unit of the outer shaft, apart from openings in the front component.

2. The endoscope according to claim 1, wherein a width of the border strip is determined by the wall thickness of the front component.

3. The endoscope according to claim 1, wherein the front component forms the entire front surface of the distal end unit of the outer shaft, except for the border strip along the edge between the mantle surface and the front surface, the border strip having a width corresponding to the wall thickness of the mantle component.

4. The endoscope according to claim 1, wherein at the edge, the front component forms an area of the mantle surface and the mantle component forms an area of the front surface of the distal end of the outer shaft.

5. The endoscope according to claim 1, wherein the front component has the shape of a surface with Gaussian curvature K=0.

6. The endoscope according to claim 1, wherein the front component is configured from an elastically reshaped metal sheet.

7. A method for producing a distal end unit configured to be joined at a distal end of a shaft tube, the shaft tube forming a majority of an outer shaft of an endoscope, wherein the distal end unit has a mantle surface and a curved front surface that border each other at an edge, the method having the following steps:
providing a mantle component;
providing a curved front component, wherein providing the front component includes the step of generating a pass-through opening that is configured at least to receive either a light outlet surface in an illuminating beam path or a window component in an observation beam path, wherein the mantle surface is formed by a surface of the mantle component and border strip of the front component, and wherein the curved front surface is formed by the front component;

joining the front component to the mantle component at an interface, a distance from the interface to the edge being no greater than a wall thickness of the mantle component or no greater than a wall thickness of the front component;

wherein the distance is measured in a direction of a local surface normal of the interface;

wherein, in the case of the edge is broken, rounded, or beveled, the distance from the interface to the edge is a distance to a line in which the mantle surface and the curved front surface intersect when the edge is not broken, rounded, or beveled, or before the edge is broken, rounded or beveled;

wherein the front component forms the entire curved front surface of the distal end unit, except for openings in the front component;

wherein the mantle component is produced separately and then joined to the shaft tube.

8. The method according to claim 7, wherein providing the front component includes the following steps:

provide a workpiece;

generate the front component from the workpiece at least either by means of erosion or by means of laser cutting.

9. The method according to claim 7, wherein providing the front component includes the following steps:

provide a metal sheet;

elastically reshape the metal sheet.

10. The method according to claim 7, wherein the joining of the mantle component and of the front component includes the following steps:

attach the front component to the mantle component;

join the front component with the mantle component along an entire interface between the mantle component and the front component.

11. A method for producing an endoscope, having the following steps:

providing a shaft tube;

producing a distal end unit configured to be disposed at a distal end of the shaft tube, wherein the distal end unit has a mantle surface and a curved front surface that border each other at an edge, the step of producing the distal end unit includes:

providing a mantle component;

providing a curved front component, wherein providing the front component includes the step of generating a pass-through opening that is configured at least to receive either a light outlet surface in an illuminating beam path or a window component in an observation beam path, wherein the mantle surface is formed by a surface of the mantle component and border strip of the front component, and wherein the curved front surface is formed by the front component;

joining the front component to the mantle component at an interface, a distance from the interface to the edge being is no greater than a wall thickness of the mantle component or no greater than a wall thickness of the front component;

wherein the distance is measured in a direction of a local surface normal of the interface;

wherein, in the case of the edge is broken, rounded, or beveled, the distance from the interface to the edge is a distance to a line in which the mantle surface and the curved front surface intersect when the edge is not broken, rounded, or beveled, or before the edge is broken, rounded or beveled;

wherein the front component forms the entire curved front surface of the distal end unit, except for openings in the front component;

wherein the mantle component is produced separately and then joined to the shaft tube.

12. An endoscope, comprising:

an outer shaft having a shaft tube and a distal end unit, a proximal border of said distal end unit being joined to a distal end of said shaft tube, said shaft tube and said distal end unit forming an exterior surface of said outer shaft, the distal end unit having a mantle surface, curved front surface, and an edge between the mantle surface and the curved front surface, such that the distal end unit includes a mantle component and a curved front component, said mantle component and said front component each having an interface in a shape of a strip, the interfaces of said mantle component and said front component being joined to one another, said front component being a curved plate, such that a distance from the interfaces the edge is no greater than a wall thickness of the mantle component or no greater than a wall thickness of the front component.

13. The endoscope according to claim 12, wherein:

said front component has a recess disposed in the front surface at a distal section of the said front component, and said mantle component has a protrusion extending from a distal border of said mantle component, said protrusion being flush with the mantle surface and configured to engage said recess of said front component such that said mantle component in an area of said protrusion forms a portion of said edge.

14. The endoscope according to claim 13, wherein the engagement of the protrusion of said mantle component with the recess of said front component provides a form-locking connection between said mantle component and said front component.

15. The endoscope according to claim 12, wherein:

said mantle component has one or more recesses in the mantle surface at the distal border of said mantle component, and said front component has one or more protrusions extending from a proximal section of said front component, said one or more protrusions of said front component being configured to engage said one or more recesses of said mantle component such that said front component in an area of said one or more protrusions forms a portion of said edge.

16. The endoscope according to claim 15, wherein the engagement of the one or more protrusions of said front component with the one or more recesses of said mantle component provides a form-locking connection between said mantle component and said front component.

* * * * *